(12) United States Patent
Alchas et al.

(10) Patent No.: US 6,569,123 B2
(45) Date of Patent: May 27, 2003

(54) PREFILLABLE INTRADERMAL INJECTOR

(75) Inventors: Paul G. Alchas, Wayne, NJ (US); Carlos E. Guillermo, Clinton, CT (US); Marina S. Korisch, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 44 days.

(21) Appl. No.: 09/834,669

(22) Filed: Apr. 13, 2001

(65) Prior Publication Data

US 2001/0056263 A1 Dec. 27, 2001

Related U.S. Application Data

(63) Continuation-in-part of application No. 09/417,671, filed on Oct. 14, 1999, now Pat. No. 6,494,865.

(51) Int. Cl.$^7$ ................................................ A61M 5/32
(52) U.S. Cl. ...................................... 604/192; 604/198
(58) Field of Search ................................ 604/117, 187, 604/192, 198, 110, 164, 165, 162

(56) References Cited

U.S. PATENT DOCUMENTS

| | | | |
|---|---|---|---|
| 1,934,046 A | 11/1933 | Demarch | 128/215 |
| 2,876,770 A | 3/1959 | White | 128/215 |
| 3,073,306 A | 1/1963 | Linder | 128/215 |
| 3,400,715 A | 9/1968 | Pederson | 128/215 |

(List continued on next page.)

FOREIGN PATENT DOCUMENTS

| | | |
|---|---|---|
| DE | 41 27 887 C1 | 1/1993 |
| EP | 0279583 B1 | 10/1993 |
| EP | 0 904 790 A2 | 3/1999 |

OTHER PUBLICATIONS

*Purified Influenza Vaccine: Clinical and Serologic Responses to Varying Doses and Different Routes of Immunization,* by C.A. Phillips, B.R. Forsyth, W.A. Christmas, D.W. Gump, E.B. Whorton, I. Rogers, and A. Rudin, from the Department of Medicine and Community Medicine, University of Vermont College of Medicine, Burlington, Vermont.

*Polyvalent Influenza Vaccine: Comparison of Jet Injection with Intradermal and Subcutaneous Syringe Methods of Administration,* authored by Mervin L. Clark, Herbert Reinhardt, M. Clinton Miller, III and Ray Wilson, Oklahoma City, Oklahoma.

*Experimental Comparison of Intradermal and Subcutaneous Vaccination with Influenza Vaccine,* from the American Journal of Medical Technology, vol. 31, Nov.–Dec. 1965, No. 6.

(List continued on next page.)

*Primary Examiner*—Manuel Mendez
(74) *Attorney, Agent, or Firm*—David M. Fortunato (57) ABSTRACT

A prefillable delivery device for administering intradermal injections includes a prefillable container adapted to store a substance. The substance is expelled through a needle cannula having a forward tip adapted to administer the intradermal injection. A limiter surrounds the needle cannula having a generally flat skin engaging surface extending in a plane generally perpendicular to the needle cannula. An insert is centrally located within the skin engaging surface and is piercable by the forward tip. A sleeve with a first end and a second end surrounds the prefillable container. The limiter is slidably inserted through the first end and the second end is affixed to a depressable plunger for expelling the substance from the container. The limiter is movable between a first position and a second position thereby exposing the forward tip and is selectively movable between a third position and a fourth position thereby concealing the forward tip.

30 Claims, 5 Drawing Sheets

U.S. PATENT DOCUMENTS

| | | | |
|---|---|---|---|
| 3,890,971 A | 6/1975 | Leeson et al. | 128/218 |
| 4,060,073 A | 11/1977 | Collica et al. | 128/1.1 |
| 4,270,537 A | 6/1981 | Romaine | 128/218 |
| 4,373,526 A | 2/1983 | King | 604/117 |
| 4,583,978 A | 4/1986 | Porat et al. | 604/208 |
| 4,596,556 A | 6/1986 | Morrow et al. | 604/70 |
| 4,769,003 A | 9/1988 | Stamler | 604/39 |
| 4,790,824 A | 12/1988 | Morrow et al. | 604/143 |
| 4,883,573 A | 11/1989 | Thomas | |
| 4,886,499 A | 12/1989 | Cirelli et al. | 604/131 |
| 4,898,588 A | 2/1990 | Roberts | 604/187 |
| 4,940,460 A | 7/1990 | Casey et al. | 604/143 |
| 4,941,880 A | 7/1990 | Burns | 604/143 |
| 4,955,871 A | 9/1990 | Thomas | |
| 4,978,344 A | 12/1990 | Dombrowski et al. | 604/198 |
| 5,015,235 A | 5/1991 | Crossman | 604/117 |
| 5,064,413 A | 11/1991 | McKinnon et al. | 604/70 |
| 5,071,353 A | 12/1991 | van der Wal | 434/262 |
| 5,137,516 A * | 8/1992 | Rand et al. | 604/136 |
| 5,141,496 A | 8/1992 | Dalto et al. | 604/117 |
| 5,190,521 A | 3/1993 | Hubbard et al. | 604/51 |
| 5,222,949 A | 6/1993 | Kaldany | |
| 5,312,335 A | 5/1994 | McKinnon et al. | 604/72 |
| 5,331,954 A | 7/1994 | Rex et al. | 128/200.22 |
| 5,334,144 A | 8/1994 | Alchas et al. | 604/68 |
| 5,339,163 A | 8/1994 | Homma et al. | 348/229 |
| 5,368,578 A | 11/1994 | Covington et al. | 604/232 |
| 5,383,851 A | 1/1995 | McKinnon, Jr. et al. | 604/68 |
| 5,417,662 A | 5/1995 | Hjerman et al. | 604/117 |
| 5,431,155 A | 7/1995 | Marelli | 128/200.14 |
| 5,437,647 A | 8/1995 | Firth et al. | 604/110 |
| 5,466,220 A | 11/1995 | Brenneman | 604/87 |
| 5,480,381 A | 1/1996 | Weston | 604/68 |
| 5,496,286 A | 3/1996 | Stiehl et al. | 604/232 |
| 5,503,627 A | 4/1996 | McKinnon et al. | 604/72 |
| 5,514,107 A | 5/1996 | Haber et al. | 604/197 |
| 5,520,639 A | 5/1996 | Peterson et al. | 604/68 |
| 5,527,288 A | 6/1996 | Gross et al. | 604/140 |
| 5,569,189 A | 10/1996 | Parsons | 604/68 |
| 5,578,014 A * | 11/1996 | Erez et al. | 604/192 |
| 5,582,598 A | 12/1996 | Chanoch | 604/208 |
| 5,599,302 A | 2/1997 | Lilley et al. | 604/68 |
| 5,649,912 A | 7/1997 | Peterson | 604/187 |
| 5,665,071 A | 9/1997 | Wyrick | 604/134 |
| 5,702,362 A | 12/1997 | Herold et al. | 604/58 |
| 5,704,911 A | 1/1998 | Parsons | 604/72 |
| 5,779,677 A | 7/1998 | Frezza | 604/134 |
| 5,873,856 A | 2/1999 | Hjertman et al. | 604/117 |
| 5,879,327 A | 3/1999 | Moreau De Farges et al. | 604/68 |
| 5,891,085 A | 4/1999 | Lilley et al. | 604/68 |
| 5,893,397 A | 4/1999 | Peterson et al. | 141/27 |
| 5,921,963 A | 7/1999 | Erez et al. | 604/192 |
| 5,944,700 A * | 8/1999 | Nguyen et al. | 604/263 |
| 5,957,897 A | 9/1999 | Jeffrey | 604/223 |
| 5,961,495 A | 10/1999 | Walters et al. | 604/208 |
| 5,993,412 A | 11/1999 | Deily et al. | 604/68 |
| 6,001,089 A | 12/1999 | Burroughs et al. | 604/506 |
| 6,004,299 A | 12/1999 | Arai et al. | 604/218 |
| 6,036,675 A | 3/2000 | Thorne et al. | 604/232 |
| 6,053,893 A | 4/2000 | Bucher | 604/131 |
| 6,083,197 A | 7/2000 | Umbaugh | 604/68 |
| 6,090,077 A | 7/2000 | Shaw | 604/195 |
| 6,090,080 A | 7/2000 | Jost et al. | 604/207 |
| 6,090,082 A | 7/2000 | King et al. | 604/234 |
| 6,093,170 A | 7/2000 | Hsu et al. | 604/110 |
| 6,112,743 A | 9/2000 | Denton | 128/200.14 |
| 6,200,291 B1 | 3/2001 | Di Pietro | 604/117 |
| 6,210,369 B1 | 4/2001 | Wilmot et al. | 604/157 |
| 6,213,977 B1 * | 4/2001 | Hjertman et al. | 604/117 |

FOREIGN PATENT DOCUMENTS

| | | |
|---|---|---|
| EP | 1066848 | 1/2001 |
| EP | 1092444 | 4/2001 |
| FR | 612 401 A1 | 10/1926 |
| GB | 725024 | 3/1955 |
| GB | 735538 | 8/1955 |
| GB | 2 206 794 A | 1/1989 |
| JP | 2000-37456 | 2/2000 |
| WO | 9309826 | 5/1993 |
| WO | WO 95/01198 | 1/1995 |
| WO | WO9713537 | 4/1997 |
| WO | WO9737705 | 10/1997 |
| WO | 9925402 | 5/1999 |
| WO | WO 99/27986 | 6/1999 |
| WO | WO 99/34850 | 7/1999 |
| WO | 9937345 | 7/1999 |
| WO | 0056384 | 9/2000 |

OTHER PUBLICATIONS

*Intradermal Influenza Immunization, Experience with Hong Kong Vaccine,* from the American Review of Respiratory Disease, vol. 103, 1971.

*Efficacy of Adsorbed Trivalent Split Infuenza Vaccine Administered by Intradermal Route,* by I. Th. Niculescu, Eugenia Zilisteanu, V. Alexandrescu, Mihaela Matepiuc, Ligia Cretescu, N. Ionescu, G. Molnar, R. Racasan and Adina Mogos, received for publication Dec. 4, 1980, from Arch. Roum. Path. Exp. Microbiol., T. 40, No. 1, pp. 67–70, Janvier–Mars, 1981.

*Efficacy of Intradermally Administered A2 Hong Kong Vaccine,* from Jama, from Jama, Jul. 6, 1970, vol. 213, No. 1.

*Comparison of Responses to Influenza,* A–New Jersey/76–A/Victoria/75 *Virus Vaccine Administered Intradermally or Subcutaneously to Adults with Chronic Respiratory Disease,* authored by F. Alexander Herbert, R. P. Bryce Larke, and Edythe L. Markstad, from the Journal of Infectious Diseases, vol. 140, No. 2, Aug. 1979.

*A Comparison of the Intradermal and Subcutaneous Routes of Influenza Vaccination with A/New Jersey/76 (Swine Flu) and A/Victoria/75: Report of a Study and Review of the Literature,* by William Halperin, MD, MPH, William I. Weiss, MD, Ronald Altman, MD, MPH, Michael A. Diamond, MD, Kenneth J. Black, BA, Alfred W. Iaci, BBA, MS, Henry C. Black, DVM and Martin Goldfield, MD, from the ALPHA Dec. 1979, vol. 69, No. 12.

*Effect of Dosage and Route of Inoculation Upon Antigenicity of Inactivated Influenza Virus Vaccine (Hong Kong Strain) in Man,* from Bull. Org. mond. Santé Bull. Wld Hlth Org. 1969, 41, 507–516.

*Comparative Analysis of Six European Influenza Vaccines,* from Eur. J. Clin. Microbiol. Infect. Dis. 1996, 15:121–127.

*Morphological and Biochemical Characterization of Infuenza Vaccines Commercially Available in the United Kingdom,* by F. Renfrey and A. Watts, from Vaccine 1994, vol. 12, No. 8.

*Influenza Immunization Policies and Practices in Japan,* from the Journal of Infectious Diseases, vol. 141, No. 2, Feb. 1980.

*Clinical Immunogenicity and Tolerance Studies of Liquid Vaccines Delivered by Jet–Injector and a New Single–Use Cartidge (Imule®): Comparison with Standard Syringe Injection,* authored by Isabelle Parent du Chatelet, Jean Lang, Martin Schlumberger, Emmanuel Vidor, Georges Soula, Alain Gene, Steven M. Standaert, Pierre Saliou and Imule® Investigators Group, Vaccine 1997, vol. 15, No. 4.

Abstract: *Does a Needleless Injection System Reduce Anxiety in Children Receiving Intramuscualr Injections?*, by Polillio AM, Kiley J, from the Pediatric Primary Care Clinic, Boston City Hospital, MA, USA. Pediatr. Nurs. 1997, Jan.–Feb.; 23(1):46–9.

Abstract: *Intradermal Administration of Viral Vaccines,* by Nagafuchi S., Kashiwagi S, Imayama S, Hayashi J, Niho Y, from Rev. Med. Virol. 1998 Apr.; 8(2):97–111.

Abstract: *Letter: Intradermal Influenza Vaccination,* by Payler DK, Skirrow MB, Br Med J Jun. 29, 1974; 2(921);727.

Intradermal Influenza Vaccination; British Medical Journal, Jun. 29, 1974.

Smith Kline Beecham Meeting Agenda.

International Search Report dated Dec. 20, 2001 for International Appln No. PCT/US01/12251.

International Search Report dated Dec. 20, 2001 for International Appln No. PCT/US01/12247.

International Search Report dated Dec. 20, 2001 for International Appln No. PCT/US01/12248.

Article: Dermal Immune System by Brian J. Nickoloff, MD, PhD.

Article: Trials of Intradermal Hepatitis B Vaccines in Gambian Children by Whittle, Lam, Ryder.

Article: Injection Technique Intradermal.

Article: The Dendritic Cell System and its Role in Immunogenicity by Ralph Steinman .

Article: Intradermal Gene Immunization: The Possible Role of DNA Uptake in the Iduction of Cellular Immunity to Viruses by: Eyal Raz et al.

Article: Clinical Do's & Don'ts—Giving Intradermal Injections by Edwina Mcconnell, RN, PhD.

Article: Monographs of the Physiological Society No. 12: Substances Producing Pain and Itch by C. A. Keele and D. Armstrong Pub: The Williams & Wilkins Company (1964).

* cited by examiner

PREFILLABLE INTRADERMAL INJECTOR

REFERENCE TO RELATED APPLICATIONS

The present application is a continuation-in-part of U.S. patent application Ser. No. 09/417,671 filed on Oct. 14, 1999 now U.S. Pat. No. 6,494,865.

FIELD OF THE INVENTION

The present invention relates generally to a prefillable delivery device for delivering substances such as drugs, vaccines and the like used in the prevention, diagnosis, alleviation, treatment or cure of diseases, and more specifically relates to a drug delivery device having a needle cannula and a limiter for engaging the surface of the skin and limiting penetration of the tip of the needle cannula into the skin. More specifically, the present invention relates to a limiter capable of fixing the orientation of the needle cannula in a generally perpendicular plane to the skin engaging surface of the limiter and capable of concealing the needle cannula subsequent to administering the intradermal injection.

BACKGROUND OF THE INVENTION

Intradermal injections are used for delivering a variety of substances. Many of these substances have proven to be more effectively absorbed into or react with the immune response system of the body when injected intradermally. Recently, clinical trials have shown that hepatitis B vaccines administered intradermally are more imunogenic if administered intramuscularly. In addition, substances have been injected intradermally for diagnostic testing, such as, for example using what is known in the art as the "Mantoux test" to determine the immunity status of the animal against tuberculosis and the immediate hypersensitivity status of Type I allergic diseases.

An intradermal injection is made by delivering the substance into the epidermis and upper layers of the dermis. Below the dermis layer is subcutaneous tissue (also sometimes referred to as the hypodermis layer) and muscle tissue, in that order. There is considerable variation in the skin thickness both between individuals and within the same individual at different sites of the body. Generally, the outer skin layer, epidermis, has a thickness between 50–200 microns, and the dermis, the inner and thicker layer of the skin, has a thickness between 1.5–3.5 mm. Therefore, a needle cannula that penetrates the skin deeper than about 3.0 mm has a potential of passing through the dermis layer of the skin and making the injection into the subcutaneous region, which may result in an insufficient immune response, especially where the substance to be delivered intradermally has not been indicated for subcutaneous injection. Also, the needle cannula may penetrate the skin at too shallow a depth to deliver the substance and result in what is commonly known in the art as a "wet injection" because of reflux of the substance from the injection site.

The standard procedure for making an intradermal injection is known to be difficult to perform, and therefore dependent upon experience and technique of the healthcare worker. This procedure is recommended to be performed by stretching the skin, orienting the bevel of a 26 Gauge short bevel needle cannula upwardly and inserting the needle cannula to deliver a volume of 0.5 ml or less of the substance into the skin of an animal with the needle cannula being inserted into the skin at an angle varying from around 10–15 degrees relative to the plane of the skin to form a blister or wheal in which the substance is deposited or otherwise contained. Accordingly, the technique utilized to perform the standard intradermal injection is difficult and requires the attention of a trained nurse or medical doctor. This procedure also makes it essentially impossible to self-administer an intradermal injection. Inserting the needle to a depth greater than about 3.0 mm typically results in a failed intradermal injection because the substance being expelled through the cannula will be injected into the subcutaneous tissue of the animal. Further, the present method is not suitable for self-administration of intradermal injections.

Further, with the advent of viral infections that are transferred through contact with bodily fluids, it is desirable to enclose a needle cannula subsequent to administering an injection. Preferably, a needle assembly should include a mechanism that is capable of enclosing a needle cannula immediately subsequent to administering the injection. If a needle is left uncovered for even a short period of time after administering an injection, such as, for example, while trying to reattach a needle cap, a biohazard exists. U.S. patent application Ser. No. 09/417,671 discloses needle assemblies having a limiter to facilitate administering an intradermal injection, the disclosed assemblies are not capable of concealing or enclosing the needle cannula after administering the injection. Therefore, it is desirable to provide a needle assembly with an integral device that is simply designed, easy to use, and readily available immediately after administering an injection.

Accordingly, there has been a need for a needle assembly of intradermal injection device providing the ability to perform an intradermal injection of substances which overcomes the problems and limitations associated with conventional needle assemblies. Further, there has been a need to provide the needle assembly with an enclosure device that is capable of enclosing a needle cannula immediately subsequent to administering the intradermal injection. The combination of these two features on the same needle assembly would provide the ability to both reduce the probability of error and pain caused from the intradermal injection and to enclose the needle cannula after the injection has been administered.

SUMMARY OF THE INVENTION AND ADVANTAGES

In contrast to the needle assemblies discussed above, the present invention both enables the administration of an intradermal injection utilizing a simplified method that reduces the probability of error and also enables the user to conceal the needle immediately after administering the injection. Specifically, The prefillable intradermal injector of the present invention for use in intradermally injecting substances into the skin of an animal includes a prefillable reservoir adapted to store a substance and having an outlet port at a first end enabling the substance to be expelled from the reservoir and a stopper in a second open end, a needle cannula defining an axis and the needle cannula in fluid communication with the reservoir to receive the substance from the outlet port and having a forward tip adapted to penetrate the skin of an animal, a limiter surrounding the needle cannula, the limiter including a generally flat skin engaging surface extending in a plane generally perpendicular to an axis of the needle cannula, and a sleeve having a first end and a second end, the sleeve surrounding and slidable relative to the reservoir along the axis and the sleeve fixed relative to the stopper whereby movement of the sleeve causes the stopper to move through the reservoir to expel the substance from the reservoir through the needle cannula.

In the preferred embodiment of the prefillable intradermal injector, the limiter is moveable axially relative to the needle cannula from a retracted position wherein the forward tip of the needle cannula extends through the limiter to an extended position wherein the needle cannula forward tip is enclosed within the limiter. Also, the forward tip of the needle cannula extends through the limiter beyond the skin engaging surface no more than from about 0.5 mm to about 3.0 mm in the retracted position of the limiter.

In addition, in the preferred embodiment, the limiter is moveable axially relative to the reservoir from a first position wherein the forward tip of the needle is located within the limiter to a second position wherein the needle extends through the limiter beyond the skin engaging surface no more than from about 0.5 to 3.0 mm, with the limiter including an axial opening therethrough receiving the forward tip of the needle cannula and the opening includes pierceable insert sealing the axial opening, and the forward tip of the needle cannula preferably extending beyond the skin engaging surface no more than from about 1.0 to 2.0 mm, and more preferably extending beyond the skin engaging surface about 1.5 mm±0.2 to 0.3 mm. Also, the forward tip of the needle cannula pierces the insert when the limiter is located in the second position thereby exposing the forward tip enabling administration of the intradermal injection.

Also, in the preferred embodiment, the limiter includes a locking arm and the sleeve includes a catch engaging the locking arm when the limiter is located in the extended position enclosing the forward tip of the needle cannula, with the locking arm including a hook disposed upon a distal end and the catch includes a slot disposed in the sleeve and the hook engaging the slot when the limiter is located in the extended position. Further, the prefillable container includes a stop to terminate movement of the limiter at the second position when moving the limiter between the first position and the second position. Still further, the prefillable intradermal injector includes a spring biasing the limiter to move from the retracted position to the extended position, with the spring preferably coiled around the reservoir. The sleeve includes a stopper engaging portion, with stopper engaging portion including a plunger rod operably connected to the second end of the sleeve.

The method of the present invention for administering an intradermal injection through a needle cannula from a prefillable intradermal injector having a substance stored in a reservoir in fluid communication with a needle cannula defining an axis, includes the steps of providing a limiter slideably disposed on the reservoir and having a generally flat skin engaging surface extending in a plane generally perpendicular to the axis of the needle cannula having a forward tip located within the limiter, moving the limiter in a first direction relative to the reservoir to expose the forward tip, expelling the substance from the reservoir through the needle cannula into the skin of an animal, and moving the limiter in a second direction relative to the reservoir to enclose the forward tip inside the limiter.

In the preferred embodiment of the method, moving the limiter in the first direction includes piercing an insert centrally located within the limiter, and depressing the skin engaging surface against the skin of the animal inserts the forward tip into the skin of the animal. In addition, the method includes locking the forward tip inside the limiter after administering the intradermal injection, with locking the forward tip inside the limiter further defined by locking the limiter in a position relative to the prefillable container. Also, the limiter limits penetration of the forward tip of the needle cannula into the dermis layer of the skin during the step of moving the limiter in the first direction, with penetration of the forward tip of the needle cannula limited to about 0.5 to 3.0 mm, and preferably limited to about 1.0 to 2.0 mm or 1.5 mm±0.2 to 0.3 mm.

Alternatively, the prefillable intradermal injector of the present invention includes a reservoir prefillable with a substance having a generally closed proximal end and an open distal end, a needle cannula having a distal end in fluid communication with the substance in the reservoir extending through the proximal end and an exposed forward tip, a stopper slideably received in the open distal end of the reservoir moveable in the reservoir to expel the substance through the forward tip of the needle cannula, and a limiter having a distal end slideably supported around the reservoir and moveable relative to the reservoir and a generally closed proximal end including a flat skin engaging surface having an opening therethrough receiving the forward tip of the needle cannula therethrough as the limiter moves relative to the reservoir and the limiter limiting extension of the forward tip of the needle cannula beyond the skin engaging surface a distance of more than 3.0 mm.

In this embodiment of the prefillable intradermal injector, the proximal end of the reservoir engages a surface of the limiter as the limiter is moved toward the reservoir, thereby limiting movement of the limiter relative to the reservoir. In addition, the intradermal injector includes a sleeve surrounding the reservoir operably fixed to the stopper whereby movement of the sleeve relative to the reservoir moves the stopper through the reservoir. Also, the opening through the proximal end of the limiter includes a pierceable closure and the forward tip of the needle cannula pierces the closure as the limiter is moved toward the reservoir, with the forward tip of needle cannula extends through the limiter beyond the skin engaging surface no more than from about 1.0 to 2.0 mm, and preferably 1.5±0.2 to 0.3 mm. Further, the intradermal injector includes a spring biased between the reservoir and the limiter moving the limiter to an extended position enclosing the forward tip of the needle cannula following injection.

The present invention provides the desirable features set forth above that are not presently included on the same needle assembly. The limiter facilitates making an intradermal injection at a generally perpendicular angle to the skin of the animal and then also conceal or enclose the needle subsequent to administering the injection.

BRIEF DESCRIPTION OF THE DRAWINGS

Other advantages of the present invention will be readily appreciated and apparent to those skilled in the art as the same becomes better understood by reference to the following detailed description when considered in connection with the accompanying drawings wherein.

DETAILED DESCRIPTION OF THE PREFERRED EMBODIMENT

An intradermal delivery device is generally shown in FIGS. 1 to 5 at 10. The device includes a sleeve 12 having a first proximate end 14 and a second distal end 16. A plurality of ribs 18 are disposed on the outside surface of the sleeve 12 to assist gripping the sleeve 12, the purpose of which will be further evident below. A limiter 20 is slidably inserted through the first end 14 of the sleeve 12.

Figure 1:
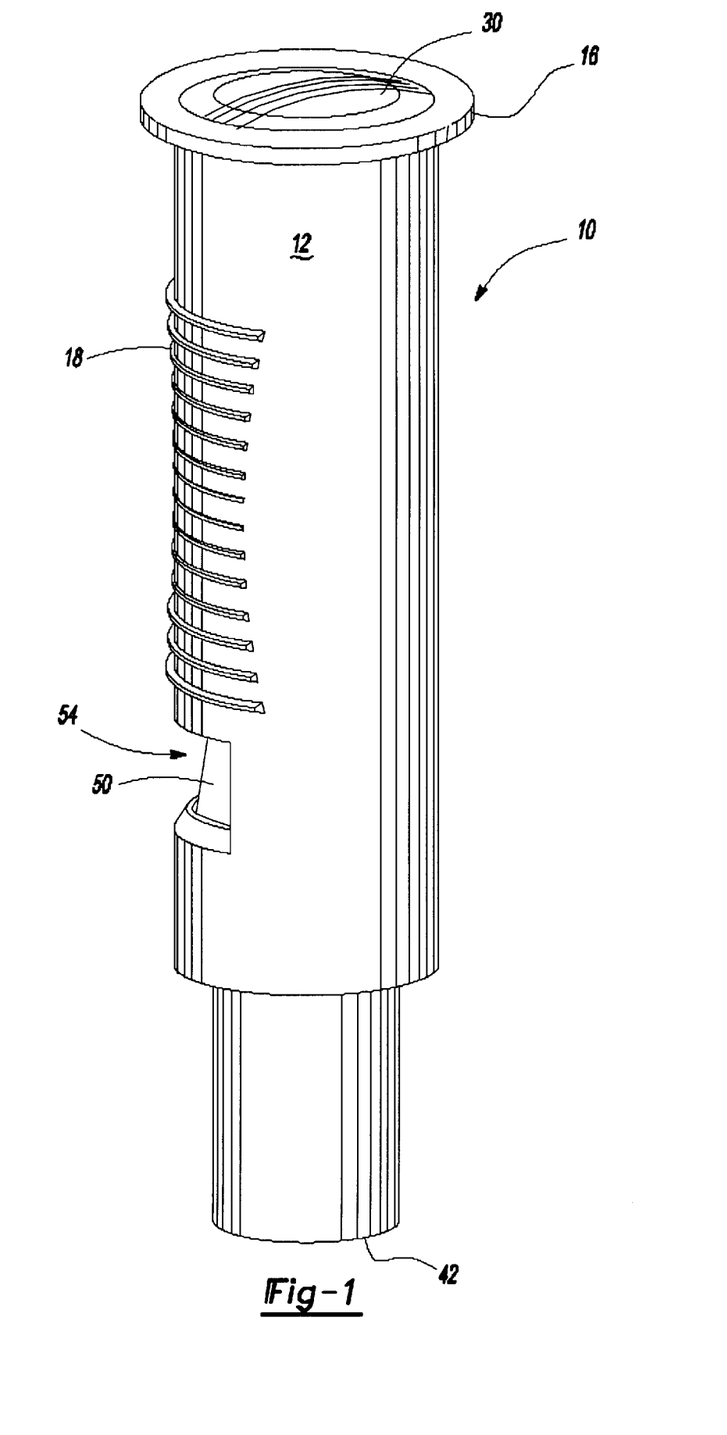
FIG. 1 is a perspective view of the intradermal delivery device of the present invention.
Figure 2:
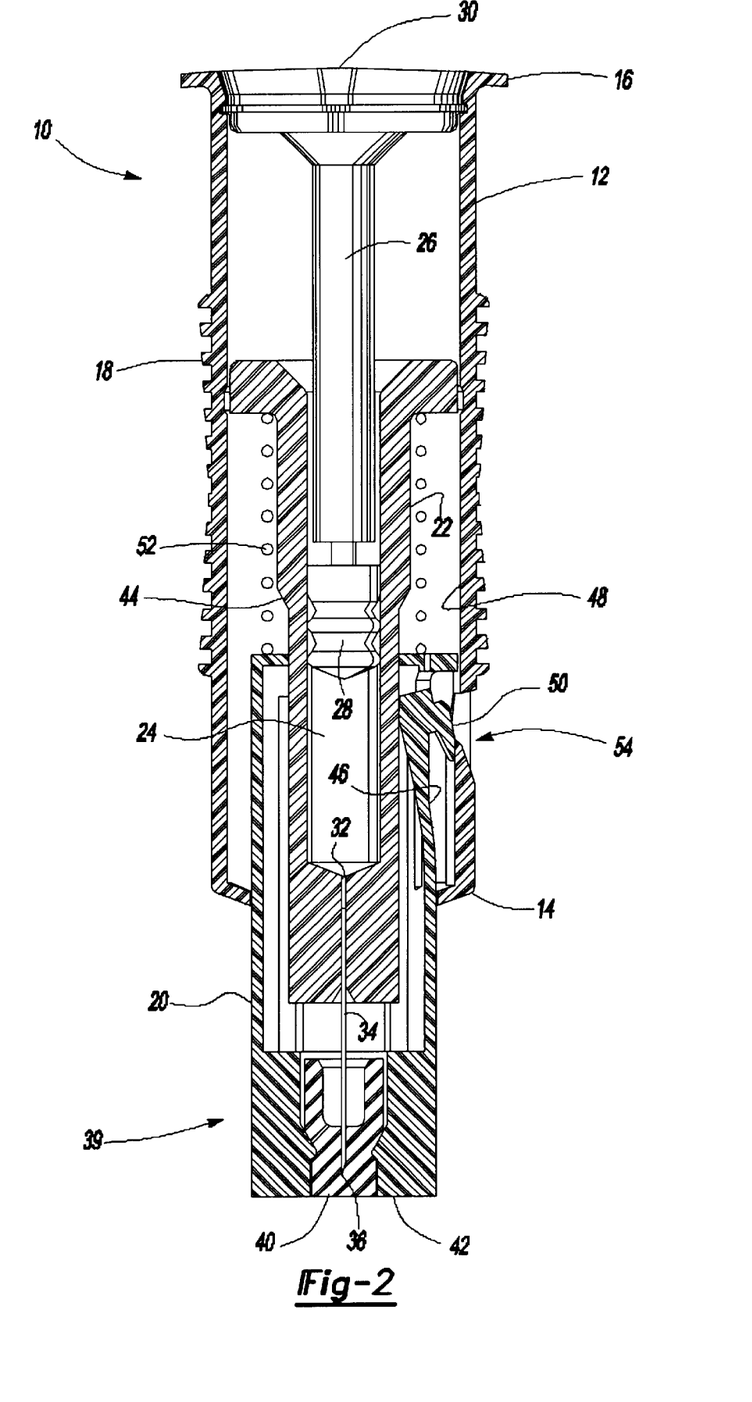
FIG. 2 is a side sectional view of the intradermal delivery device showing the limiter in the first position.

Referring to FIG. 2, a prefillable container 22 is disposed inside the sleeve 12. The prefillable container 22 includes a reservoir 24 adapted to store a substance intended for intradermal delivery into the skin of an animal. The substance comprises drugs, vaccines, and the like that are known to be absorbed significantly better in the dermis layer of the skin of the animal as opposed to the subcutaneous region of the animal.

Also, the substance intradermally delivered in accordance with the method of the present invention is selected from the group consisting of drugs, vaccines and the like used in the prevention, diagnosis, alleviation, treatment, or cure of disease, with the drugs including Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhoea, asthma, atheroschlerosis malaria, E-coli, Alzheimers, H. Pylori, salmonella, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents.

The present invention also includes the use of the above substances in the preparation of a filled device for making an intradermal injection into the skin of an animal. Accordingly, as disclosed in the U.S. patent application, Ser. No. 09/835,243, filed Apr. 13, 2001, entitled "METHOD OF INTRADERMAL INJECTING SUBSTANCES," the disclosure of which is hereby incorporated by reference, the device may be prefilled in accordance with the steps disclosed therein.

A plunger 26 is slidably received in the reservoir 24 through the open end. A stopper 28 seals the reservoir 24 and is selectively movable by the plunger 26 for expelling the substance from the prefillable container reservoir 22. A manual activation flange or button 30 is disposed at an opposite end of the plunger 26 from the stopper 28. The flange 30 is fixedly attached to the second end 16 of the sleeve 12, the purpose of which will be explained below.

The prefillable container includes an outlet port 32 through which the substance is expelled from the reservoir 24. A needle cannula 34 is affixed to the prefillable container 22 and is in fluid communication with the outlet port 32. The needle cannula 34 may be attached to the prefillable container 22 with an adhesive, a mechanical, interference fit, or an equivalent known method of attachment.

The needle cannula 34 includes a forward tip 36 that is adapted to administer an intradermal injection. Preferably, the forward tip 36 includes a beveled edge 38 ranging in length from approximately 0.8 mm to 1.0 mm. More preferably, the beveled edge 38 includes a length of approximately 0.9 mm. A standard beveled tip length ranges from approximately 1.3 mm to 1.6 mm. The reduced length of the present beveled edge 38 reduces the potential of the needle cannula 34 piercing through the dermis layer of the skin of the animal and resulting in the substance from the reservoir 24 being injected into the subcutaneous region of the animal.

The prefillable container reservoir 22 is slidably received within the limiter 20. The limiter includes a pierceable elastomeric insert 40 into which the forward tip 36 of the needle cannula 34 is embedded (FIG. 1) when the limiter is in a first position 39. Preferably, the insert 40 is formed from an elastomer or a thermal plastic elastomer. The insert 40 seals the needle cannula 34 preventing the prefilled substance from leaking from the reservoir 24 through the cannula 34 prior to administering the intradermal injection.

The elastomeric insert 40 is centrally located in a skin engaging surface 42 on the limiter 20. The skin engaging surface 42 is generally planar, annular and continuous and provides a stable placement of the delivery device 10 against an animal skin. The width of the annular skin engaging surface is preferably at least 5 mm. Further, the planar skin engaging surface 42 extends generally perpendicular to the axis of the needle cannula.

Figure 3:
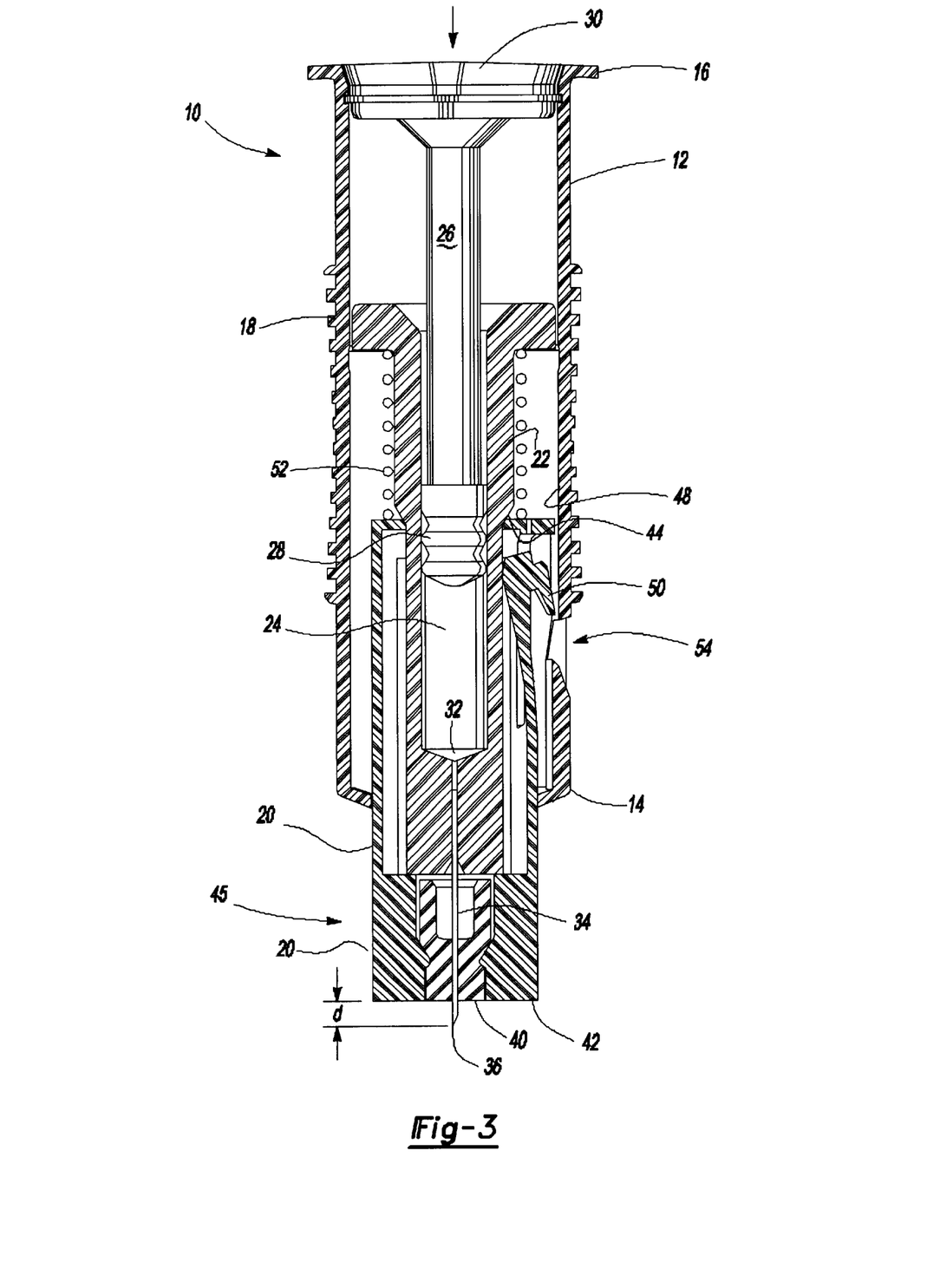
FIG. 3 is a side sectional view of the intradermal delivery device showing the limiter in the second position.

As shown in FIG. 3, the forward tip 36 of the needle cannula 34 extends beyond the skin engaging surface 42 a length "d" determined to facilitate administering an intradermal injection. The forward tip 36 extends past the skin engaging surface 42 a distance of approximately 0.5 mm. to 3 mm preferably 1.0 mm to 2.0 mm, and most preferably 1.5 mm±0.2 to 0.3 mm. The preferred needle size is a small gauge hypodermic needle, commonly known as a 30 Gauge or a 31 Gauge needle.

As shown in FIGS. 2 through 5, the prefillable container 22 is slidably received within the limiter 20 inside the sleeve 12. To force the forward tip 36 of the needle cannula 34 through the insert 40, force is applied to the activation flange 30 of the plunger 26. Accordingly, the limiter 20 slides into the sleeve 12 reducing the length the limiter 20 is exposed outside the sleeve 12. The prefillable container 22 is fixedly attached to the sleeve 12 so that the prefillable container 22 is stationary relative to the sleeve 12 when the limiter 20 or the plunger 26 is moving. Thus, when the limiter 20 moves relative to the sleeve 12, the limiter 20 is also moving relative to the prefillable container 22. The prefillable container 22 includes a stop 44 represented in the Figures as the surface of the prefillable container 22 having an increased diameter. The stop 44 terminates movement of the limiter 20 in a second position 45 as shown in FIG. 3 exposing a predetermined length "d" of the needle cannula 34 relative to the skin engaging surface 42.

Figure 4:
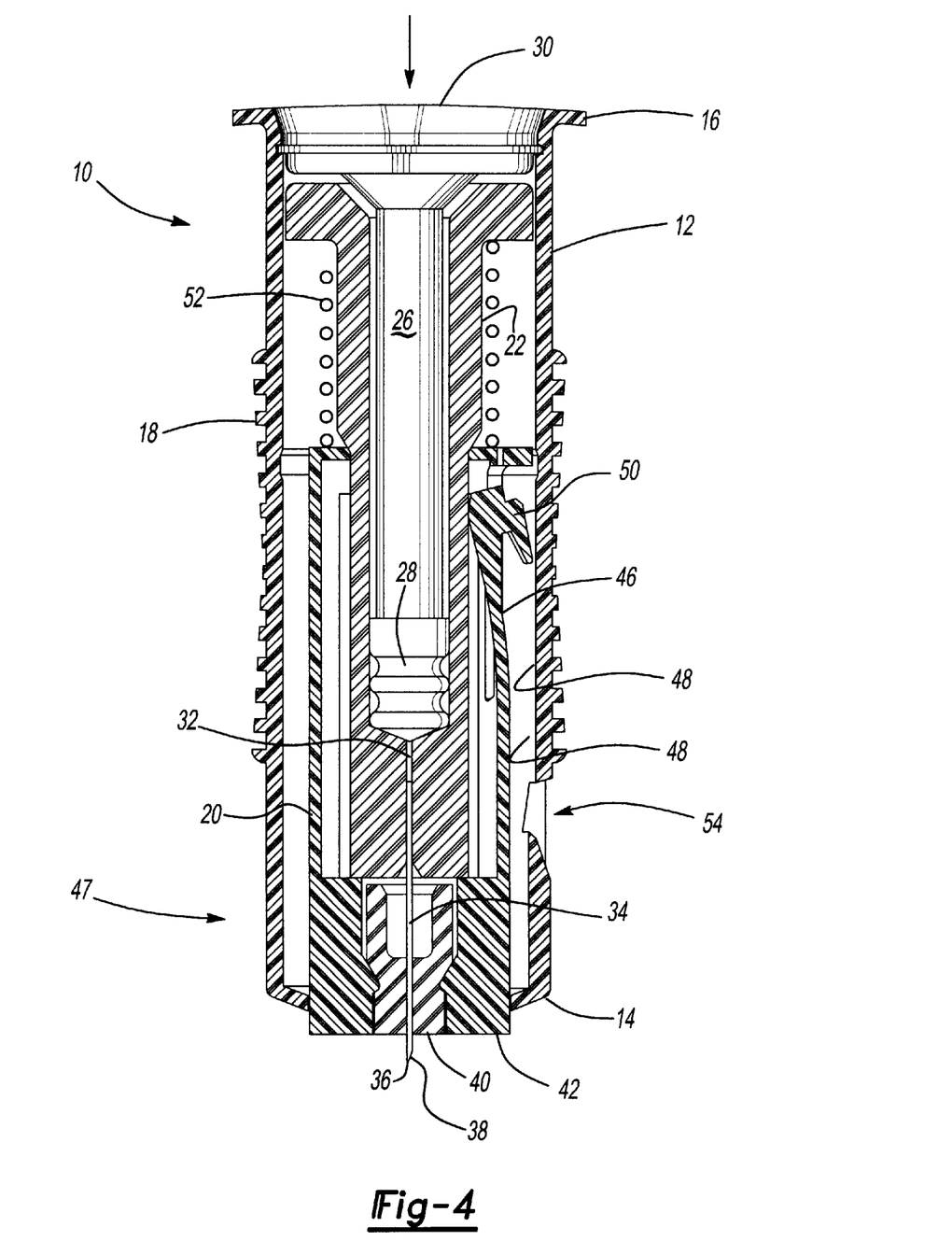
FIG. 4 is a side sectional view of the intradermal delivery device showing the limiter in the third position.

Referring to FIG. 4, continued force on the actuation flange 30 drives the plunger 26 inwardly of the prefillable container 22 expelling the substance from the reservoir 24 through the needle cannula 34 into the skin of the animal, thereby moving the intradermal delivery device 10 from the second position 45 to a third position 47.

As shown in FIGS. 2 through 5, the limiter 20 includes a locking arm 46 oriented generally parallel to the prefillable container 22 and being biased outwardly from the limiter 20 toward an inner surface 48 of the sleeve 12. The locking arm 46 includes a catch 50 represented in the Figures as a hook that slides freely inside the sleeve 12 when moving the limiter 20 from the first position 39 through the third position 47.

Figure 5:
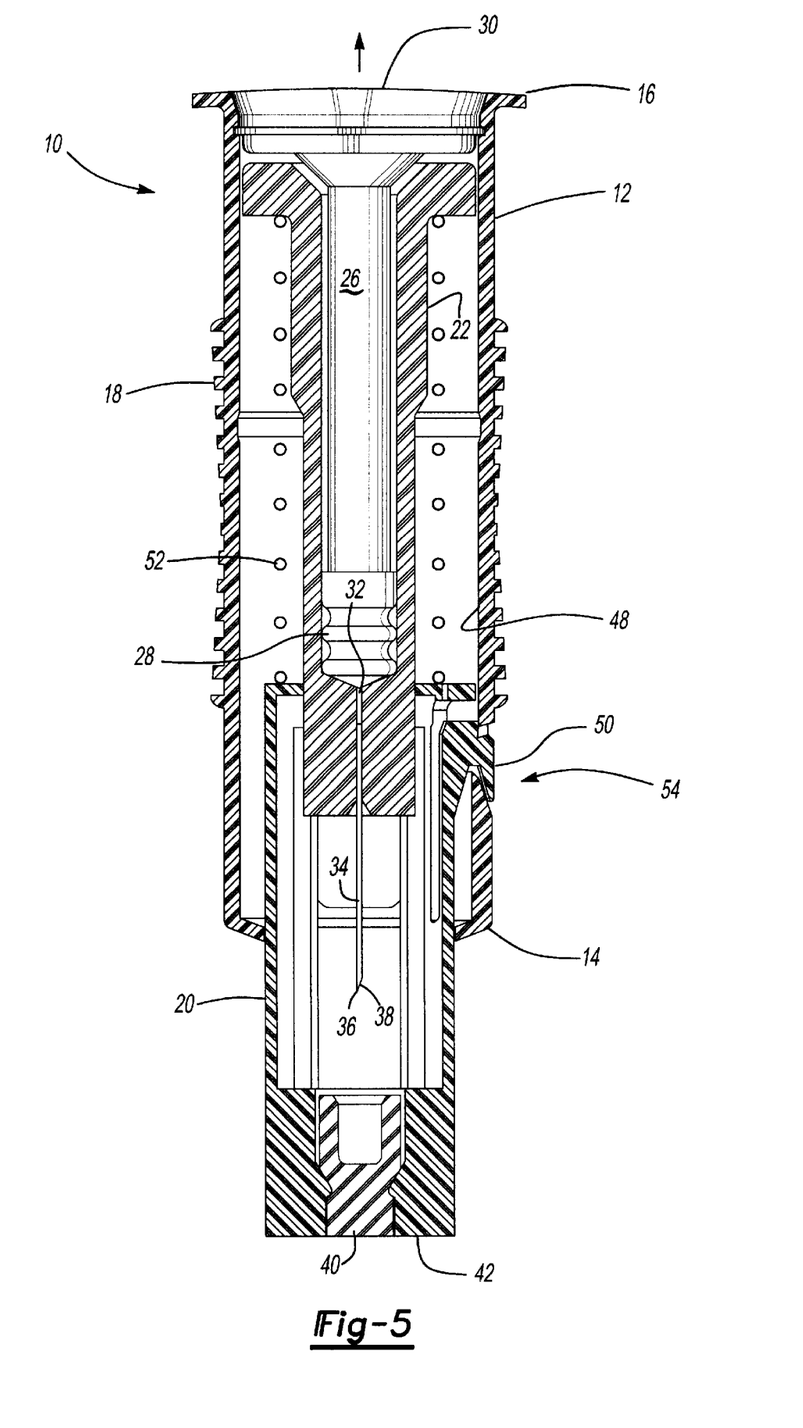
FIG. 5 is a side sectional view of the intradermal delivery device showing the limiter in the fourth position.

Referring to FIG. 5, subsequent to administering a intradermal injection, the limiter 20 is movable from the third position 47 to a fourth position 49, to enclose the needle cannula 34 inside the limiter 20. A spring 52 is optionally disposed inside the sleeve 12 and biases the limiter 20 outwardly of the sleeve 12. Preferably, the spring 52 is coiled around the prefillable container 22 and is compressed between the activation flange 30 and the limiter 20. Upon releasing the force from the activation flange 30, the spring 52 forces the limiter 20 outwardly of the sleeve 12, which withdraws the needle cannula 34 back into the limiter 20, thereby moving the device from the third position 47 to the fourth position 49. When the limiter 20 has reached the fourth position, the catch 50 engages a slot 54 disposed in the sleeve 12 in a manner that locks the limiter 20 to prevent the limiter from being moved from the fourth position 49 back to the third position 47 in which the needle tip would be exposed.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

What is claimed is:

1. A prefillable intradermal injector for use in intradermally injecting substances into the skin of an animal comprising:

a prefillable reservoir adapted to store a substance and having an outlet port at a first end enabling the substance to be expelled from said reservoir and a stopper in a second open end;

a needle cannula defining an axis and said needle cannula in fluid communication with said reservoir to receive the substance from said outlet port and having a forward tip adapted to penetrate the skin of an animal;

a limiter surrounding said needle cannula, said limiter including a generally flat skin engaging surface extending in a plane generally perpendicular to an axis of said needle cannula, said limiter limiting penetration of said forward tip of said needle cannula into the dermis layer of the skin of the animal; and a sleeve having a first end and a second end, said sleeve surrounding and slidable relative to said reservoir along said axis and said sleeve fixed relative to said stopper whereby movement of said sleeve causes said stopper to move through said reservoir to expel said substance from said reservoir through said needle cannula.

2. The prefillable intradermal injector as defined in claim 1, wherein said limiter is moveable axially relative to said needle cannula from a retracted position wherein said forward tip of said needle cannula extends through said limiter to an extended position wherein said needle cannula forward tip is enclosed within said limiter.

3. The prefillable intradermal injector as defined in claim 2, wherein said forward tip of said needle cannula extends through said limiter beyond said skin engaging surface no more than from about 0.5 mm to about 3.0 mm in said retracted position of said limiter.

4. The prefillable intradermal injector as defined in claim 1, wherein said limiter is moveable axially relative to said reservoir from a first position wherein said forward tip of said needle is located within said limiter to a second position wherein said needle extends through said limiter beyond said skin engaging surface no more than from about 0.5 to 3.0 mm.

5. A prefillable intradermal injector as set forth in claim 4, wherein said limiter includes an axial opening therethrough receiving said forward tip of said needle cannula and said opening includes pierceable insert sealing said axial opening.

6. The prefillable intradermal injector as set forth in claim 4, wherein said forward tip of said needle cannula extends beyond said skin engaging surface no more than from about 1.0 to 2.0 mm.

7. The prefillable intradermal injector as set forth in claim 4, wherein said forward tip of said needle cannula extending beyond said skin engaging surface about 1.5 mm±0.2 to 0.3 mm.

8. The prefillable intradermal injector as set forth in claim 5, wherein said forward tip of said needle cannula pierces said insert when said limiter is located in said second position thereby exposing said forward tip enabling administration of the intradermal injection.

9. A prefillable intradermal injector as set forth in claim 2, wherein said limiter includes a locking arm and said sleeve includes a catch engaging said locking arm when said limiter is located in said extended position enclosing said forward tip of said needle cannula.

10. A prefillable intradermal injector as set forth in claim 9, wherein said locking arm includes a hook disposed upon a distal end and said catch includes a slot disposed in said sleeve, said hook engaging said slot when said limiter is located in said extended position.

11. A prefillable intradermal injector as set forth in claim 4, wherein said prefillable container includes a stop to terminate movement of said limiter at said second position when moving said limiter between said first position and said second position.

12. A prefillable intradermal injector as set forth in claim 2, further comprising a spring biasing said limiter to move from said retracted position to said extended position.

13. A prefillable intradermal injector as set forth in claim 12, wherein said spring is coiled around said reservoir.

14. A prefillable intradermal injector as set forth in claim 1, wherein said sleeve includes a stopper engaging portion.

15. A prefillable intradermal injector as set forth in claim 14, wherein said stopper engaging portion includes a plunger rod operably connected to said second end of said sleeve.

16. A method of administering an intradermal injection through a needle cannula from a prefillable intradermal injector having a substance stored in a reservoir in fluid communication with a needle cannula defining an axis, comprising the steps of:

providing a limiter slideably disposed on said reservoir and having a generally flat skin engaging surface extending in a plane generally perpendicular to said axis of said needle cannula having a forward tip located within said limiter;

moving said limiter in a first direction relative to said reservoir to expose said forward tip, wherein said limiter limits penetration of the forward tip of said needle cannula into the dermis layer of the skin;

expelling the substance from said reservoir through said needle cannula into the skin of an animal; and moving said limiter in a second direction relative to said reservoir to enclose said forward tip inside said limiter.

17. A method as set forth in claim 16, wherein said step of moving said limiter in said first direction includes piercing an insert centrally located within said limiter.

18. A method as set forth in claim 16, further including the step of depressing said skin engaging surface against the skin of the animal thereby inserting the forward tip into the skin of the animal.

19. A method as set forth in claim 16, further including the step of locking said forward tip inside said limiter after administering the intradermal injection.

20. A method as set forth in claim 19, wherein said step of locking said forward tip inside said limiter is further defined by locking said limiter in a position relative to said prefillable container.

21. A method as set forth in claim 16, wherein said penetration of said forward tip of said needle cannula is limited to about 0.5 to 3.0 mm.

22. A method as set forth in claim 16, wherein said penetration of said forward tip of said needle cannula is limited to about 1.0 to 2.0 mm.

23. A method as set forth in claim 16, wherein said penetration of said forward tip of said needle cannula is limited to 1.5 mm±0.2 to 0.3 mm.

24. A prefillable intradermal injector, comprising:

a reservoir prefillable with a substance having a generally closed proximal end and an open distal end;

a needle cannula having a distal end in fluid communication with said substance in said reservoir extending through said proximal end and an exposed forward tip;

a stopper slideably received in said open distal end of said reservoir moveable in said reservoir to expel said substance through said forward tip of said needle cannula; and a limiter having a distal end slideably supported around said reservoir and moveable relative to said reservoir and a generally closed proximal end including a flat skin engaging surface having an opening therethrough receiving said forward tip of said needle cannula therethrough as said limiter moves relative to said reservoir and said limiter limiting extension of said forward tip of said needle cannula beyond said skin engaging surface a distance of more than 3.0 mm.

25. The prefillable intradermal injector as set forth in claim 24, wherein said proximal end of said reservoir engages a surface of said limiter as said limiter is moved toward said reservoir, thereby limiting movement of said limiter relative to said reservoir.

26. The prefillable intradermal injector as set forth in claim 24, wherein said intradermal injector includes a sleeve surrounding said reservoir operably fixed to said stopper whereby movement of said sleeve relative to said reservoir moves said stopper through said reservoir.

27. The prefillable intradermal injector as set forth in claim 24, wherein said opening through said proximal end of said limiter includes a pierceable closure and said forward tip of said needle cannula pierces said closure as said limiter is moved toward said reservoir.

28. The prefillable intradermal injector as set forth in claim 24, wherein said forward tip of needle cannula extends through said limiter beyond said skin engaging surface no more than from about 1.0 to 2.0 mm.

29. The prefillable intradermal injector as set forth in claim 28, wherein said forward tip of said needle cannula extends through said limiter 1.5±0.2 to 0.3 mm.

30. The prefillable intradermal injector as set forth in claim 24, further comprising a spring biased between said reservoir and said limiter moving said limiter to an extended position enclosing said forward tip of said needle cannula following injection.

* * * * *